US00PP32582P3

(12) United States Plant Patent
van Zoest

(10) Patent No.: US PP32,582 P3
(45) Date of Patent: Dec. 8, 2020

(54) ***CLEMATIS* PLANT NAMED 'ZO11112'**

(50) Latin Name: ***Clematis* hybrid**
Varietal Denomination: Zo11112

(71) Applicant: J. van Zoest Beheer B.V., Boskoop (NL)

(72) Inventor: Jan van Zoest, Boskoop (NL)

(73) Assignee: J. VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 16/602,139

(22) Filed: Aug. 13, 2019

(65) Prior Publication Data

US 2020/0305320 P1 Sep. 24, 2020

(30) Foreign Application Priority Data

Mar. 18, 2019 (QZ) ..... PBR 2019/0727

(51) Int. Cl.
*A01H 5/02* (2018.01)
*A01H 6/72* (2018.01)

(52) U.S. Cl.
USPC ..... Plt./228
CPC ..... *A01H 6/72* (2018.05)

(58) Field of Classification Search
USPC ..... Plt./226, 228
See application file for complete search history.

(56) References Cited

PUBLICATIONS

Horticulture Connected, Novelties at Plantarium 2018—Part 3. https://horticultureconnected.ie/news/ornamentals/novelties-at-plantarium-2018-part-3/. 3 pages (Year: 2018).*

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of hybrid *Clematis* plant named 'Zo11112' that is characterized by its free flowering habit, its climbing habit, its flowers that are dark violet in color, its flowers that are facing upright, and its cold hardiness at least to U.S.D.A. Zone 6.

2 Drawing Sheets

Botanical classification: *Clematis* hybrid.
Variety denomination: 'Zo11112'.

CROSS REFERENCE TO A RELATED APPLICATION

This application claims priority to European Community Plant Variety Office (CPVO) Plant Breeder's Rights Application No. 2019/0727 filed on Mar. 18, 2019, the entire contents of which is incorporated by reference herein.

BACKGROUND OF THE INVENTION

The present invention relates to a new and distinct cultivar of *Clematis* of hybrid origin and will be referred to hereafter by its cultivar name 'Zo11112'. 'Zo11112' is an herbaceous perennial grown for use as a landscape plant.

The new Invention arose from an ongoing controlled breeding program in Boskoop, The Netherlands. The objective of the breeding program is to develop hybrid cultivars of *Clematis* with unique and superior garden attributes. In particular, to develop a cultivar that is very free flowering and climbing.

The Inventor made a cross in 2007 between an unnamed proprietary plant in the Inventor's breeding program, reference no. 19960159, as the female parent and reference no. 19960212 as the male parent. The Inventor selected 'Zo11112' in 2011, as a single unique plant amongst the seedlings that resulted from the above cross.

Asexual propagation of the new cultivar was first accomplished by softwood stem cuttings under the direction of the Inventor in Boskoop, The Netherlands in 2011. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish *Clematis* 'Zo11112' as a unique cultivar of *Clematis*.

1. 'Zo11112' exhibits a free flowering habit.
2. 'Zo11112' exhibits a climbing habit.
3. 'Zo11112' exhibits flowers that are dark violet in color.
4. 'Zo11112' exhibits flowers that are facing upright.
5. 'Zo11112' exhibits cold hardiness at least to U.S.D.A. Zone 6.

The female parent of 'Zo11112' differs from 'Zo11112' in having flowers that are white in color, upright held flower buds, solitary flowers only and in having cold hardiness only to U.S.D.A. Zone 9. The male parent of 'Zo11112' differs from 'Zo11112' in having flowers that are pink in color, nodding in aspect and bell-shaped and in having cold hardiness to U.S.D.A. Zone 5. 'Zo11112' can be most closely compared to the *Clematis* cultivars 'Venosa Violacea' (not patented) and 'Zo09088' (not patented). Both are similar to 'Zo11112' in having upright flowers that violet in color and nodding flower buds. 'Venosa Violacea' differs from 'Zo11112' in having tepals that have prominent white colored veins and filaments that are green-white in color. 'Zo09088' differs from 'Zo11112' in having tepals with prominent veins and filaments that are green-white at the base, violet towards the anther and dark violet below the anther.

STATEMENT DESIGNATING A GRACE PERIOD UNDER 102(B)(1)

The Applicant claims prior art exemption under 35 U.S.C. 102(b)(1) for disclosure and/or sales prior to the filing date but less than one year prior to the effective filing date if need be. Information about the claimed plant was obtained from a direct or indirect disclosure from the Inventor; including but not limited to disclosures on websites by J Van Zoest, Plantarium, Nijssen tuin, Taylors *Clematis*, Thorncroft *Clematis* and Royal Horticultural Society.

BRIEF DESCRIPTION OF THE DRAWINGS

The accompanying colored photographs illustrate the overall appearance and distinct characteristics of the new *Clematis*. The photographs were taken of a three-year-old plant as grown outdoors in a 20-liter pot in Boskoop, The Netherlands.

The photograph in FIG. 1 provides a view of 'Zo11112' in bloom.

Figure 1:
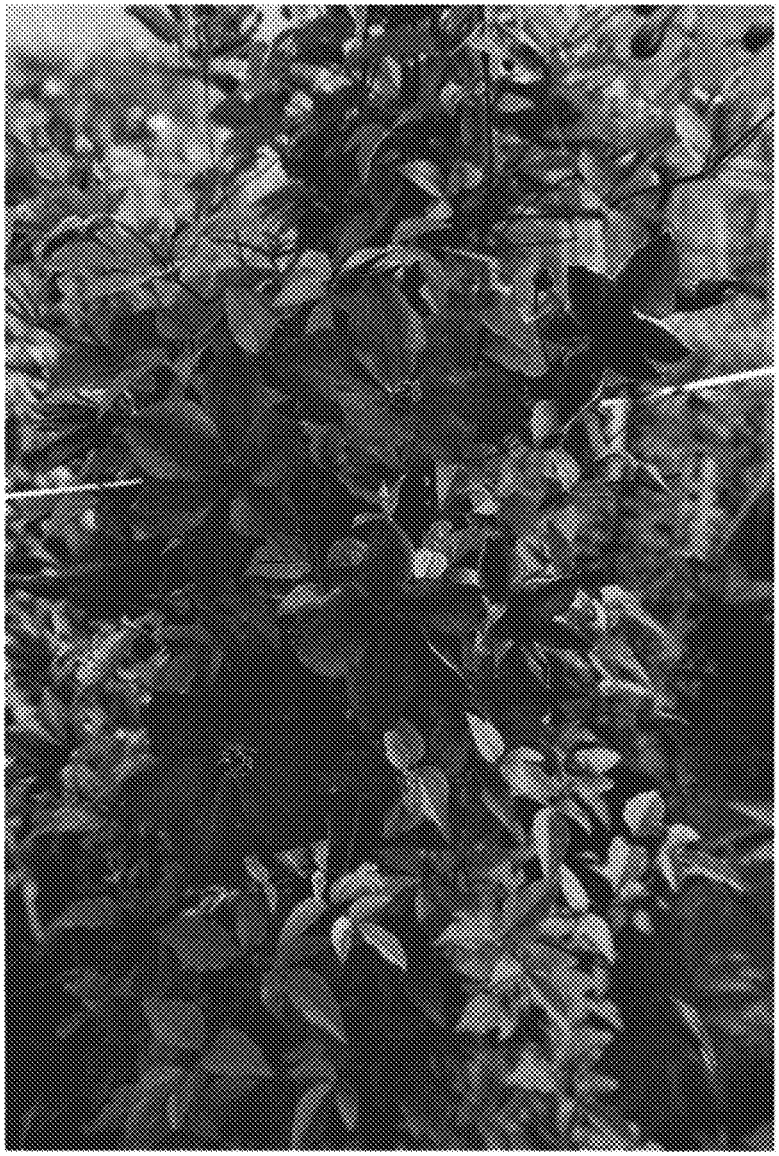
Figure 2:
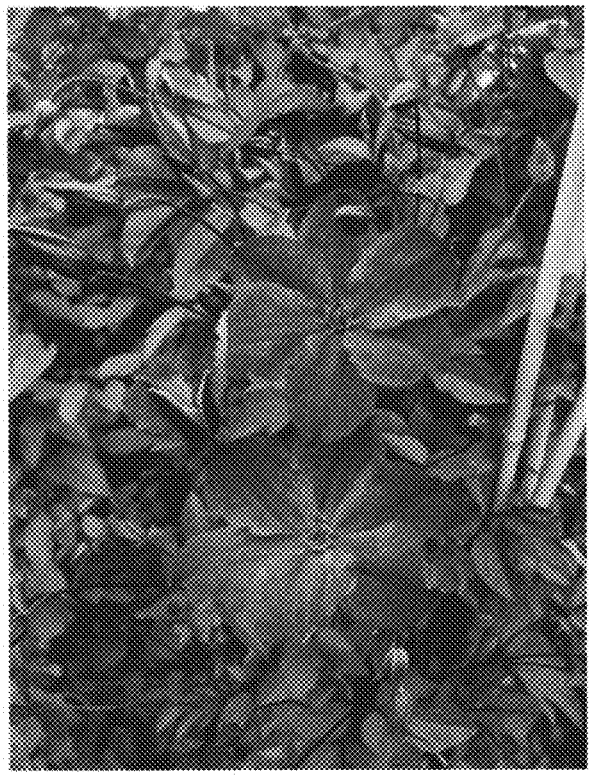

The photograph in FIG. 2 provides a close-up view of the flowers and flower buds of 'Zo11112'.

Figure 3:
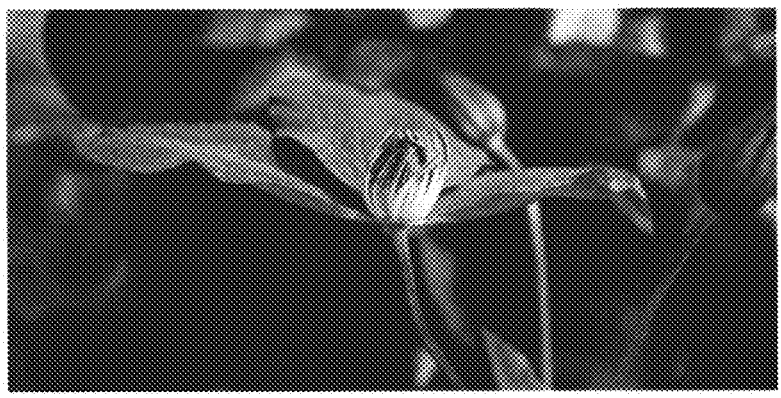

The photograph in FIG. 3 provides a close-up view of a cross section of a flower of 'Zo11112'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of three-year-old plants as grown outdoors in 20-Liter rose containers in Boskoop, The Netherlands. The phenotype of the new cultivar may vary with variations in environmental, climatic and cultural conditions, as the cultivar has not been tested under all possible environmental conditions. The color determination is in accordance with The 2015 Colour Chart of the Royal Horticultural Society, London, England, except where general color terms of ordinary dictionary significance are used.

General description:

- *Blooming period*.—June into September in The Netherlands, freely flowering.
- *Plant type*.—Deciduous, blooms on new shoots, viticella type.
- *Plant habit*.—Climbing.
- *Height and spread*.—A three-year-old plant reaches an average of 3 m in height and 60 cm in width when pruned in late winter.
- *Cold hardiness*.—At least to U.S.D.A. Zone 6.
- *Diseases and pests*.—No disease or pest problems have been observed, however no susceptibility or resistance to specific causative agents have been identified.
- *Root description*.—Fleshy, 163C with tips 155C in color.
- *Propagation*.—Softwood stem cuttings.
- *Time required for root initiation*.—Roots develop in 5 weeks in summer under greenhouse conditions.
- *Time required for root development*.—75 to 90 days to fully develop a 7-cm container from a 5 cm cutting.
- *Growth rate*.—Moderate.

Stem description:

- *Shape*.—Round with 6 ribbed angles.
- *Stem color*.—Young; 143C, ribs 59A, mature; 183A.
- *Stem size*.—Up to 3 m in length, up to 0.4 mm in diameter.
- *Stem surface*.—Young; pubescent with short hairs; 156D in color, mature; sparsely pubescent with short hairs.
- *Internode length*.—Up to 9 cm.
- *Strength*.—Very strong and flexible.
- *Branching*.—From the base.

Foliage description:

- *Leaf arrangement*.—Opposite.
- *Division*.—Leaf; pinnate, leaflet; simple with lower pair occasionally sub-ternate.
- *Leaf size*.—Up to 18 cm in length and 13 cm in width.
- *Leaf attachment*.—Petiolate.
- *Leaf fragrance*.—Sharp (unpleasant) fragrance.
- *Shape*.—Ovate.
- *Leaflet size*.—Terminal; up to 6 cm in length and up to 3 cm in width.
- *Leaflet shape*.—Terminal leaflet; lanceolate, side leaflet; lanceolate to ovate.
- *Leaflet base*.—Side leaflets; oblique, terminal leaflets; sub-obtuse.
- *Leaflet apex*.—Acuminate.
- *Leaflet venation*.—Distinctly coarse, netted veins with deeper veins, upper surface 138B in color, lower surface 138A in color.
- *Leaflet quantity*.—3 to 5.
- *Leaflet margin*.—Entire to cleft.
- *Leaflet surface*.—Upper and lower surface; mostly glabrous, slightly glossy and sparsely pubescent.
- *Leaf color*.—Young upper surface; 146A, young lower surface; 138A, mature upper surface; NN137A, tinged 59A, mature lower surface; 138A.
- *Petioles*.—Up to 6 cm in length, 1 mm in diameter, 146A in color, round and slightly canaliculate in shape, aspect is straight to outward, surface is mostly glabrous with a few short hairs.
- *Petiolules*.—Rounded and slightly canaliculate in shape, 146A in color, sometimes slightly articulate below the leaflet, terminal leaflet up to 2 cm in length, side leaflets up to 1.5 mm in length, both 8 mm in diameter, straight to strongly curling, surface is sparsely pubescent.

Inflorescence description:

- *Inflorescence type*.—3-flowered dichasial cyme and solitary.
- *Inflorescence arrangement*.—Terminal and axillary on young shoots, flowering from bottom to top.
- *Inflorescence size*.—Up to 20 cm in length, 20 cm in width and 5 cm in depth when a 3-flowered cyme.
- *Peduncles*.—Up to 9 cm in length and 1.2 mm in width, N77A in color, round to very slightly ribbed in shape, surface sparsely pubescent, strong.
- *Pedicels*.—Up to 10 cm in length, average of 1 mm in diameter, N77A in color, round in shape and slightly ribbed, surface is sparsely hairy, strong.

*Flower buds*.—Nodding and becoming more upright when the buds start to open, lanceolate in shape, acuminate apex, obtuse base, up to 3 cm in length and 1.5 cm in diameter, N92A in color, surface sparsely pubescent with short hairs on seams.

*Flower fragrance*.—None.

*Lastingness of the flowers*.—Individual flowers last 2 to 3 weeks.

*Flower quantity*.—20 to 50 flowers per plant.

*Flower type*.—Single.

*Flower aspect*.—Upright.

*Flower shape*.—Open campanulate to spreading.

*Flower size*.—Up to 8 cm in diameter and 2 cm in depth.

*Flower sex*.—Bisexual.

*Receptacle*.—144C in color and 3 mm in diameter.

*Bracts*.—Simple, ovate to broadly ovate in shape, lanceolate in shape, up to 3.5 cm in length and 2.5 cm in width, acute apex, margins are entire, obtuse base, both surfaces mostly glabrous with a few sparse hairs, color; upper surface 146A with veins 138A, lower surface 138A with veins 146A.

*Tepal number*.—Average of 6.

*Tepal shape*.—Broadly elliptic.

*Tepal aspect*.—Spreading.

*Tepal apex*.—Acute to short mucronate.

*Tepal base*.—Broadly cuneate and widely overlapping.

*Tepal margin*.—Slightly ruffled.

*Tepal surface*.—Upper surface; glabrous, lower surface; middle section has a few sparse hairs, margins are villous.

*Tepal color*.—Upper and lower surface when opening; N92 and N89A, upper surface when fully open; N92A, N89A, and striped 71B especially towards apex, lower surface when fully open; 3 ribs N92A, between the ribs N92D, margins N92D.

*Tepal size*.—Up to 4.5 cm in length and an average of 4 cm in width.

*Petaloid staminodes*.—None observed.

Reproductive organs:

*Gynoecium*.—Covered by outer stamens forming a pistil-like urn shape, average of 30 to 40 pistils, up to 9 mm in length, ovary; 144D in color and covered with silver pubescent hairs 202B in color, style; 145C in color, surface is silvery plumose 202B in color, stigma; slightly bent outwards and slightly club-shaped, N92A in color, glabrous surface.

*Androecium*.—50 to 75, filaments; up to 5 mm in length, 1 mm in width and linear in shape, surface is glabrous with pubescence below the anther, 145C in color, anthers; 4 mm in length, 0.8 mm in width, linear in shape, and 145C in color, glabrous surface, pollen; 4D in color and low in quantity, connective; straight in aspect, 59A in color, glabrous surface.

*Seed*.—Seed head; up to 2 cm in diameter, globular in shape, usually not developed by self-pollination, seed; 0 to 5, 4 mm in length, 6 mm in width, 144C to 144A in color, sparsely pubescent, seed style; up to 1.2 cm in length, 144C in color with rim 144A and tiny spots of 59A towards the style, surface is sparsely pubescent with silver hairs 202C in color, seed stigma; strongly bent and 84D in color.

It is claimed:

1. A new and distinct cultivar of *Clematis* plant named 'Zo11112' as herein illustrated and described.

* * * * *